United States Patent
Liddell

(10) Patent No.: US 11,103,442 B2
(45) Date of Patent: Aug. 31, 2021

(54) MOISTURIZING COSMETIC COMPOSITION COMPRISING FATTY ACIDS, AND USES THEREOF

(71) Applicant: Sherrie Liddell, Georgetown, TX (US)

(72) Inventor: Sherrie Liddell, Georgetown, TX (US)

(*) Notice: Subject to any disclaimer, the term of this patent is extended or adjusted under 35 U.S.C. 154(b) by 286 days.

(21) Appl. No.: 16/276,644

(22) Filed: Feb. 15, 2019

(65) Prior Publication Data

US 2020/0261350 A1    Aug. 20, 2020

(51) Int. Cl.
*A61K 8/92* (2006.01)
*A61Q 5/00* (2006.01)
*A61Q 5/12* (2006.01)
*A61K 8/362* (2006.01)

(52) U.S. Cl.
CPC .............. *A61K 8/922* (2013.01); *A61K 8/362* (2013.01); *A61Q 5/002* (2013.01); *A61Q 5/12* (2013.01); *A61K 2800/5922* (2013.01)

(58) Field of Classification Search
CPC ................................................... A61K 8/922
See application file for complete search history.

(56) References Cited

U.S. PATENT DOCUMENTS

2019/0282479 A1* 9/2019 Schroeder .............. A61K 8/375

FOREIGN PATENT DOCUMENTS

WO    WO-2011113501 A1 * 9/2011 ............. A61K 8/922

OTHER PUBLICATIONS

WO-2011113501 Machine translation (C) 2021 Clarivate Analytics.*
Fregnosi et al, Brazilian oils and butters: The effect of different fatty acid chain composition on human hair physiochemical properties. International Journal of Cosmetic Science, 32(2), 160-160. Mar./Apr. 2009.
Speranza et al. Improving the chemical properties of Buriti oil (*Mauritia flexuosa* L.) by enzymatic interesterification. Grasas Y Aceites 69 (4) Oct.-Dec. 2018, e282, ISSN-L: 0017-3495, https://doi.org/10.3989/gya.0229181.
Jhon Alejandro Avila Ramírez et al. Simple citric acid-catalyzed surface esterification of cellulose nanocrystals, Carbohydrate Polymers 157, (2017) 1358-1364.
Ezekwe. The Use of Natural Ingredients in the Treatment of Alopecias with an Emphasis on Central Centrifugal Cicatricial Alopecia. J Clin Aesthet Dermatol. 2020;13(8):23-27.

* cited by examiner

*Primary Examiner* — Kortney L. Klinkel
(74) *Attorney, Agent, or Firm* — Ingenium Patents LLC; Peter R Kramer

(57) ABSTRACT

A cream to be applied topically to the hair and scalp in order to infuse moisture. The present invention effectuates this capability through a mixture of a raw material blend, in a chemical composition' proportion that brings about effective results. The prevailing ingredients in the finished product are pumpkin seed oil (*Cucurbita pepo*), rosehip seed oil (*Rosa canina* L.), mango butter (*Mangifera indica*), and citric acid.

5 Claims, No Drawings

MOISTURIZING COSMETIC COMPOSITION COMPRISING FATTY ACIDS, AND USES THEREOF

BACKGROUND OF THE INVENTION

Field of the Invention

The present invention relates to a specific natural butter for cosmetic use in hair, on the scalp, or on other areas of personal preference, wherein chemical interesterification takes place with the mango butter, and the pumpkin and rosehip seed oils.

The invention further relates to self-emulsifying with essentially, a lipophilic formulation wherein fatty acids hydrate hair and skin with emollient action.

This invention relates to the technical sector of the cosmetic industry wherein the technological blending of a solid to semi-solid, fatty acid with a liquid fatty acid component has high lipophilic affinity as a cosmetic oil-in-oil unsaturated fatty blend.

This invention correlates to technology of transesterification of natural or plant-based pumpkin and rosehip seed oils to work with exotic mango butter, whereforto, this blend has never been done and provides benefits to cosmetic formulations.

Although natural butters and plant-based carrier oils have been used historically since the mid 1990's in cosmetic applications, no prior art exists with the combinatory use of these raw materials' and their synergistic lipophilic interaction to exert an emollient affect.

OBJECTS OF THE INVENTION

It is a primary object to the present invention in which the raw material combination has a synergistic lipophilic affect that can moisturize hair, the scalp, or body hair; there is no intended use for pubic hair.

It is another object of the present invention to provide a reaction product that is derived from a physiochemical interaction between a natural butter and a plant-based carrier oil to produce a cosmetic affect with moisture-based applications.

SUMMARY OF THE INVENTION

This invention relates to a physiochemical blending of unique compositions for oil-to-oil binding by interesterification to affect moisture content of hair, the scalp, and other body hair of personal preference; however, it is not intended for pubic hair use.

This invention describes a finished product that has cohesive physiochemical blending.

This invention correlates that the finished product blend has stability due to innate antioxidant characteristics of blend components.

DETAILED DESCRIPTION OF THE INVENTION

The invention gives a finished product with the appearance of a resultant yellowish with green tinge color by the nature of the raw materials used, as its physical description.

The invention describes a resultant finished product as a creamy formulation with moisturizing effects on the skin and hair areas of the body; but it is not intended for pubic hair use.

The invention gives the following chemical component descriptions:

Pumpkin Seed Oil or Fatty Add

It's composition of matter is described as Extra Virgin Organic or Organic Pumpkin Seed Oil Crude, or *Cucurbita pepo* Seed Oil, cold-pressed, unrefined (virgin); greenish brown oily liquid with characteristic taste and odor, stable under normal conditions, and for cosmetic applications.

Rosehip Seed CO2

It's composition of matter is described as Organic, *Rosa canine* L., or Rosehip Seed CO2 Oil, Carrier Oil; or Extract or Pressed Oil, deep brownish-red oily liquid; carrier oil for safe use in body or skin care, undiluted; certified organic (USDA NOP), Kosher, and Halal; *Rosa canina* L. contains a mixture of *Rosa moschata* and *Rosa rubiginosa*, and fragrant.

Mango Butter

It's composition of matter is described as *Mangifera indica* (Mango) Seed Butter, natural, refined, light yellow color, a solid at room temperature, with high oxidative stability properties, bulk, contains high level of non-saponifiables, an additive, is a soft butter, has a sweet smell, is a fatty acid, is an emollient, and is commonly used in cosmetics.

Citric Acid

It's composition of matter is described as a crystalline solid, white, 99.9% (rounded to 100% purity), food grade; recommended for cosmetic and personal-care use, and it is described in the literature as being a natural preservative.

This product is capable of being effective during a normal shelf life based upon the properties of the raw materials used.

Making Process

This invention is formulated by aseptically and incrementally adding 46 fluid ounces of mango butter (about 78% by volume), 9 fluid ounces of pumpkin seed oil (about 15% by volume), ⅞ teaspoon of rose hips seed CO2 oil (about 0.25% by volume); and by adding 6 tablespoons of triturated citric acid, as needed (about 7% by volume).

The intermediate finished product is mixed well with a mixer.

The final blend product is blended to smoothness and desired consistency, with constant monitoring of the mixture in a blender.

The final finished product' targeted total blend time is 6 hours.

Using Process

For use on the hair, scalp, or any skin area of the body that contains hair; but it is not intended for use in the pubic hair area; and to moisturize hair and skin in these said areas.

Literature Research

Mango Butter is a natural antioxidant as an Oleyl alcohol or emulsion stabilizer.[1,2,3] "Antioxidants are man-made or natural (pure) substances that may prevent or delay some types of cell damage."[4]

Mango Butter is lipophilic and has better absorption. It can absorb into cells.[5,6]

Pumpkin seed oil is an antioxidant and fatty acid (as is Mango Butter) with Vitamin E.[7,8,9] Fatty acids have a nature to act as an emollient with moisturizing properties of the skin as well as the hair.[10,11]

The butter blends combining effects are possible through interesterification.[12] Oils and butters produce a physiochemical property on hair.[13]

Rosehip seed oil is fragrant and has antioxidant properties.[14]

Citric acid is a natural preservative.[15]

REFERENCES

[1] Jin J., Jin, Q., et al. (2018 January 16). *Mango kernel fat fractions as potential healthy food ingredients: A review*. Retrieved from Https://pubchem.ncbi.nim.nih.gov/search/#query=Mango%20Butter&page=2

[2] Dhara, R., Bhattacharyya, D. K., et al. (2010 January 1). *Analysis of sterol and other components present in unsoponifiable matters of mahua, sal and mango kernel oil*. Retrieved from Https://pubchem.ncbi.nlm.nih.gov/search/#query=Mango%20Butter&page=2

[3] Oleyl Alcohol (Created: Mar. 26, 2005; last Updated: Feb. 23, 2019). Retrieved from Https://pubchem.ncbi.nlm.nih.gov/compound/oleyl_alcohol#section=Top

[4] Antioxidants. (last Updated: Jan. 30, 2019; List Reviewed: Dec. 26, 2017). Retrieved from Https://medlineplus.gov/antioxidants.html

[5] Upadhyay, K., Gupta, N. K., et al. (2012 September). *Development and characterization of phyto-vesicles of β-Sitosterol for the treatment of androgenetic alopecia*. Retrieved from Https://link.springer.com/article/10.1007%2Fs00403-011-1199-8

[6] Sitosterol. Retrieved from Https://pubchem.ncbi.nlm.nih.gov/compound/222284#section=Human-Metabolite-Information

[7] Chouaibi, M. (2018 November). *Profile characterization of pumpkin (Cucurbita maxima) seed oils: Extraction and kinetic stability*. Retrieved from Https://www.researchgate.net/publication/329140544_Profile_characterization_of_pumpkin_Curcubita_maxima_seed_oils_Extraction_and_kinetic_stability

[8] Kirnak, H., Sipahioglu, O., et al. (2019 February). *Variations in oil, protein, fatty acids and vitamin E contents of pumpkin seeds under deficit irrigation*. Retrieved from Https://www.researchgate.net/publication/331023302_Variations_in_oil_protein_fatty_acids_and_vitamin_E_contents_of_pumpkin_seeds_under_deficit_irrigation

[9] Lieb, V., Kronmueller, A., et al. (2019 January). *Fatty acids, triacylglycerols, and thermo behavior of various mango (Mangifera indica L.) kernel fats*. Retrieved from Https://www.researchgate.net/publication/327181612_Fatty_acids_triacylalycerols_and_thermal_behaviour_of_various_mango_Manaifera_indica_L_kernel_fats

[10] Burnett, C., Bergfeld, W., et al. (2017 November). *Safety Assessment of Plant-Derived Fatty Acid Oils*. Retrieved from Https://www.researchgate.net/publication/321851653

[11] Terashi, H., Izumi, K., et al. (2000 September 24). *Human stratified squamous epithelia differ in cellular fatty acid composition*. Retrieved from Https://www.ncbi.nlm.nih.gov/pubmed/10960775

[12] Speranza, P., Gomes, T. S. N., et al. (2018 October). *Improving the chemical properties of Buriti oil (Mauritio flexuosa L.) by enzymatic interesterification*. Retrieved from Https://www.researchgate.net/Publication/328106311_Improving_the_chemical_properties_of_Buriti_oil_Mauritia_flexuosa_L_by_enzymatic_interesterification

[13] Fregonisi, A., Scanavez, C., et al. (2009 March-April). *Brazilian oils and butters: the effect of different fatty acid chain composition on human hair physiochemical properties*. Retrieved from Https://www.ncbi.nlm.nih.gov/pubmed/19450426

[14] Jemaa, H. B., Jemia, A. B., et al. (2017 January 13). *Antioxidant Activity And A-Amylase Inhibitory Potential of Rosa Canina L*. Retrieved from Https://www.ncbi.nlm.nih.gov/pubmed/28573216

[15] Pastor-Nieto, M A, Alcantara-Nicolas, F., et al. (2017 October). *Preservatives in Personal Hygiene and Cosmetic Products, Topical Medications, and Household Cleaners in Spain*. Retrieved from Https://www.ncbi.nlm.nih.gov/pubmed/28673419

I claim:

1. A method of making a moisturizing cosmetic composition comprising combining about 78% by volume mango butter, about 15% by volume pumpkin seed oil, about 0.25% by volume rose hip seed CO2 oil, and about 7% by volume citric acid and blending the resulting mixture to smoothness.

2. The method of making a moisturizing cosmetic composition of claim 1 further comprising wherein the blending step is carried out in a blender for 6 hours.

3. A method of moisturizing hair, scalp, and/or body comprising applying a composition comprising about 78% by volume mango butter, about 15% by volume pumpkin seed oil, about 0.25% by volume rose hip seed CO2 oil, and about 7% by volume citric acid to the hair, scalp and/or body.

4. A composition for moisturizing hair, scalp and/or body comprising about 78% by volume mango butter, about 15% by volume pumpkin seed oil, about 0.25% by volume rose hip seed CO2 oil, and about 7% by volume citric acid.

5. A blended composition for moisturizing hair, scalp and/or body comprising about 78% by volume mango butter, about 15% by volume pumpkin seed oil, about 0.25% by volume rose hip seed CO2 oil, and about 7% by volume citric acid, wherein said about 78% by volume mango butter, about 15% by volume pumpkin seed oil, about 0.25% by volume rose hip seed CO2 oil, and about 7% by volume citric acid are blended together in a blender for 6 hours.

* * * * *